(12) United States Patent  
Breed et al.

(10) Patent No.: US 7,935,061 B1  
(45) Date of Patent: May 3, 2011

(54) METHOD AND APPARATUS FOR MONITORING PHYSIOLOGICAL CONDITIONS

(76) Inventors: David Breed, Spicewood, TX (US); William Alexander, Spicewood, TX (US); Alfonso Cuevas, Austin, TX (US)

( * ) Notice: Subject to any disclaimer, the term of this patent is extended or adjusted under 35 U.S.C. 154(b) by 1334 days.

(21) Appl. No.: 11/431,051

(22) Filed: May 9, 2006

(51) Int. Cl.
*A61B 5/02* (2006.01)
*A61B 5/021* (2006.01)
*A61B 5/026* (2006.01)

(52) U.S. Cl. ........................................ 600/485; 600/500

(58) Field of Classification Search ................... 600/485, 600/486, 481, 490, 500, 502, 504, 506
See application file for complete search history.

(56) References Cited

U.S. PATENT DOCUMENTS

| | | | | | |
|---|---|---|---|---|---|
| 3,742,937 | A | * | 7/1973 | Manuel et al. ................. | 600/503 |
| 5,316,008 | A | * | 5/1994 | Suga et al. ..................... | 600/513 |
| 5,453,628 | A | * | 9/1995 | Hartsell et al. .................. | 257/76 |
| 6,171,253 | B1 | * | 1/2001 | Bullister et al. ............... | 600/486 |
| 6,196,974 | B1 | * | 3/2001 | Miwa ............................. | 600/490 |
| 2008/0287813 | A1 | * | 11/2008 | Kirstein et al. ............... | 600/488 |

OTHER PUBLICATIONS

Baxter, Larry K.; "Capacitive Sensors: Design and Applications"; IEEE Press Series on Electronics Technology, Robert J. Hernick, Series Editor; IEEE Industrial Electronics Society, Sponsor; pp. 45-47, 96-105, 121-125, 196-214; 1997.
Baxter, L.K.; "Capacitive Sensors"; www.capsense.com/capsense-wp.pdf; copyright Jun. 26, 2000, revised Jul. 20, 2000; pp. 1-17.
24-Bit Capacitance-to-Digital Converter with Temperature Sensor: AD7746; Analog Devices, P.O. Box 9106, Norwood, MA 02062-9106; www.analog.com/UploadedFiles/Data_Sheets/21450359AD7745_6_0.pdf; pp. 1-28, 2005.

* cited by examiner

*Primary Examiner* — Charles A Marmor, II
(74) *Attorney, Agent, or Firm* — Winstead P.C.

(57) ABSTRACT

The invention concerns a physiological monitoring device that, in one embodiment, comprises a capacitive sensor. The sensor comprises a first plate, a second plate and a dielectric medium coupled to the first plate and second plate. A power source charges the sensor to generate an initial capacitance. A band couples the sensor to a blood vessel of a patient. For example, the blood vessel can be located in the umbilical cord of a human baby. An impulse from the blood vessel exerts pressure against the second plate of the sensor and consequently generates a first capacitance. A controller monitors the patient's physiological measurement by detecting the generation of the first capacitance.

13 Claims, 9 Drawing Sheets

METHOD AND APPARATUS FOR MONITORING PHYSIOLOGICAL CONDITIONS

BACKGROUND INFORMATION

1. Technical Field

The present invention relates to apparatuses and methods for monitoring physiological conditions of a patient.

2. Description of the Related Art

In various medical environments, technology for monitoring physiological conditions like pulse rate and blood pressure are inadequate. For example, many such devices are cumbersome and lack portability. For example, in neonatal environments, medical personnel may wish to monitor the pulse located in the child's umbilical cord. This need occurs during delivery and resuscitation of newborn infants. To monitor the pulse, a technician often uses the fingers on his left hand to locate the pulse. Then, with his right hand, the technician taps out loud in synchrony with the pulse. Doing so conveys the pulse rate to the rest of the medical team. This procedure underutilizes the skills of the technician, is costly, inaccurate and also leads to a more crowded surgical environment.

As another example of shortcomings in present physiological monitors, continuous long-term blood pressure monitoring is traditionally very burdensome and inefficient. Sphygmomanometers are only used for intermittent monitoring. For example, to monitor blood pressure with a typical sphygmomanometer, the inflatable cuff is wrapped around the patient's arm and in then inflated to achieve a high pressure. The cuff is then slowly deflated to determine the patient's systolic and diastolic blood pressure. Due to the need for continuous inflation and deflation of the cuff, and the inconvenience associated with such actions, sphygmomanometers are best-suited for short-term monitoring.

Fluid-filled transducers can also be used for monitoring pressure in the short-term. These transducers are, however, costly and invasive to the patient. For example, a portion of the transducer can be placed directly in the blood stream of the patient. Such invasiveness can lead to infection. In addition, invasive procedures are uncomfortable for patients and require a skilled medical practitioner to perform them. Thus, invasive procedures are inadequate for patients that wish to monitor their blood pressure at home without professional assistance. Furthermore, the invasive nature of transducers can lead to bleeding, infection and clotting of the artery which can, in turn, lead to life-threatening complications. Medications must consequently be used to decrease blood clotting. These medications, however, carry significant potential side effects and can aggravate bleeding.

Therefore, an improved apparatus and method for continuously monitoring physiological conditions (e.g., pulse rate, blood pressure) is needed. Such an apparatus and method should be reliable, easily transportable, inexpensive, minimally invasive to the patient, accurate and not overly burdensome for medical personnel or patients.

SUMMARY DESCRIPTION

One embodiment of the invention concerns a method for determining a physiological measurement comprising the various steps. One step concerns operatively coupling a capacitive sensor to a pulsating blood vessel of a patient. The sensor includes a first plate, a second plate, and a dielectric medium that is operatively coupled to the first and second plates. The dielectric medium includes a material that enables the first plate and second plate to move relative to one another when pressure from the pulsating blood vessel is exerted on the second plate. In addition to coupling the sensor to a blood vessel, an electric potential is impressed across the first and second plates of the sensor to generate an initial capacitance. This initial capacitance is detected. Furthermore, a first capacitance, generated in response to a first pressure from a first pulse from the pulsating blood vessel, is detected. Furthermore, a physiological measurement of the patient is detected in response to detecting the second capacitance. The physiological measurement can include, for example, blood pressure and/or pulse rate.

Another embodiment of the invention includes steps such as (i) detecting a baseline blood pressure (Baseline BP) using a manometer, (ii) detecting a first minimum capacitance generated in response to a first pressure from a blood vessel; (iii) detecting a first maximum capacitance generated in response to the first pressure; (iv) detecting a baseline peak-to-peak blood pressure (Baseline peak-to-peak BP) by determining a difference between the first minimum capacitance and the first maximum capacitance; (v) detecting a second minimum capacitance generated in response to a second pressure from a second pulse from the pulsating blood vessel; (vi) detecting a second maximum capacitance generated in response to the second pressure; (vii) detecting a new peak-to-peak blood pressure (New peak-to-peak BP) by determining a difference between the second minimum capacitance and the second maximum capacitance; and (viii) detecting a new blood pressure of said patient (New BP) from the equation: (New BP)= (Baseline BP)*(New peak-to-peak BP)/(Baseline peak-to-peak BP).

Other embodiments of the invention comprise detecting first and second capacitances generated in response to first and second pressures from first and second pulses from a pulsating blood vessel. Blood pressure can be calculated using a moving window comprised of the first and second capacitances.

Additional embodiments of the invention concern detecting first and second capacitances generated in response to first and second pressures from first and second pulses from a pulsating blood vessel. A pulse rate can then be detected from the first and second capacitances.

In one embodiment of a capacitive sensor, the sensor's first plate is tubular, enclosed at least one end, and substantially surrounds the sensor's second plate. In yet another embodiment of a capacitive sensor, the sensor comprises a first, second and third plate. Still another embodiment of the invention uses multiple capacitive sensors.

The foregoing has outlined rather broadly the features of the present invention in order that the detailed description of the invention that follows can be better understood. Additional features and advantages of the invention will be described hereinafter, which form the subject of the claims of the invention.

BRIEF DESCRIPTION OF THE DRAWINGS

For a more complete understanding of the present invention, and the advantages thereof, reference is now made to the following description taken in conjunction with the accompanying drawings, in which:

FIG. 10 is a flow chart illustrating steps for monitoring physiological conditions using one embodiment of a capacitive sensor.

DESCRIPTION OF THE EMBODIMENT(S)

One embodiment of the invention concerns a method for determining a physiological measurement of a patient. That measurement can be, for example, pulse rate and/or blood pressure. The method comprises several steps that can be conducted in a variety of sequences. For example, a user might first couple a capacitive sensor to his wrist, thereby coupling the sensor to a pulsating blood vessel such as the radial and/or ulnar arteries.

Figure 1:
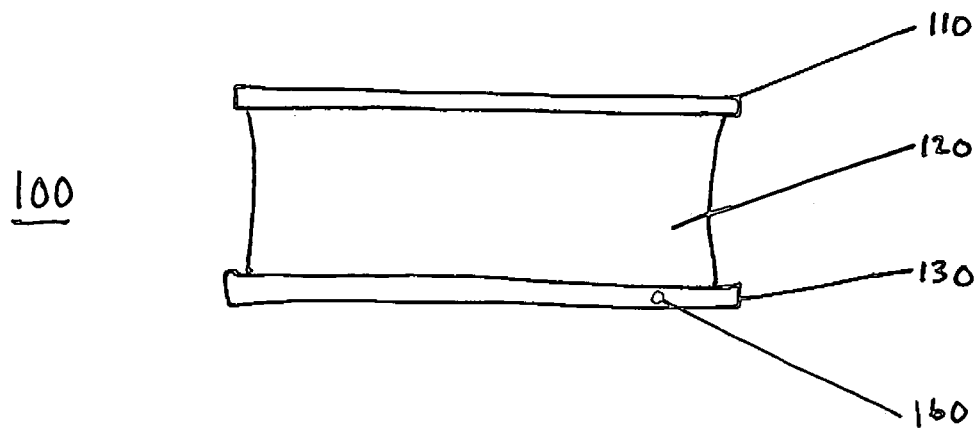
FIG. 1 is a side view of one embodiment of a capacitive sensor.

As indicated in FIG. 1, one embodiment of the sensor 100 includes a first plate 110, a second plate 130, and a dielectric medium 120 in between the first plate and second plate. The plates can comprise conductive surfaces such as, for example, flexible copper foil. The dielectric medium 120 is composed of a material that enables the first plate 110 and the second plate 130 to move relative to one another when pressure from a pulsating blood vessel is exerted against the second plate. In other words, as the heart beats, the blood vessel will pulsate. As the vessel pulsates, it will become engorged with blood and exert pressure against the second plate, causing the second plate to move relative to the first plate. For example, the second plate can move closer to the first plate. See, e.g., FIG. 3. The movement of the second plate may be very small.

The dielectric medium 320 can be air or any number of other dielectrics such as polyurethane foam, ⅛" to ¼" thick. One example of such foam includes models 87035K41 and 87035K42, available from McMaster-Carr, P.O. Box 4355 Chicago, Ill. 60680-4355, (630) 833-0300. If air is chosen, flexible, airtight members can join the first and second plates. Thus, the first and second plates can move relative to one another while still maintaining an airtight compartment for the air dielectric.

Figure 2:
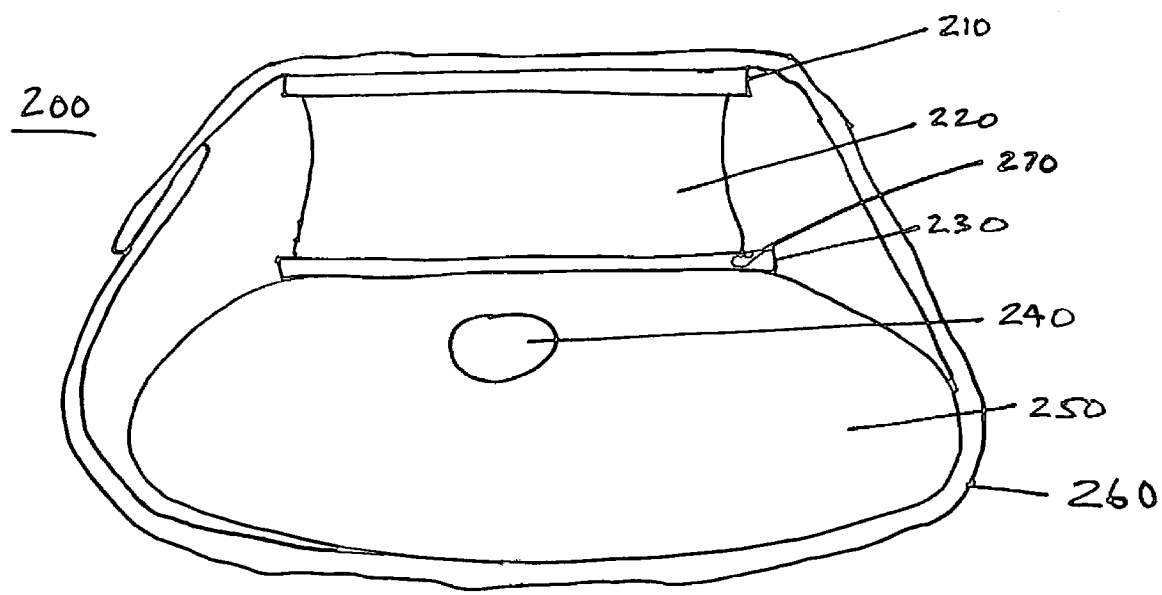
FIG. 2 is a side view of an alternative embodiment of a capacitive sensor.
Figure 4:
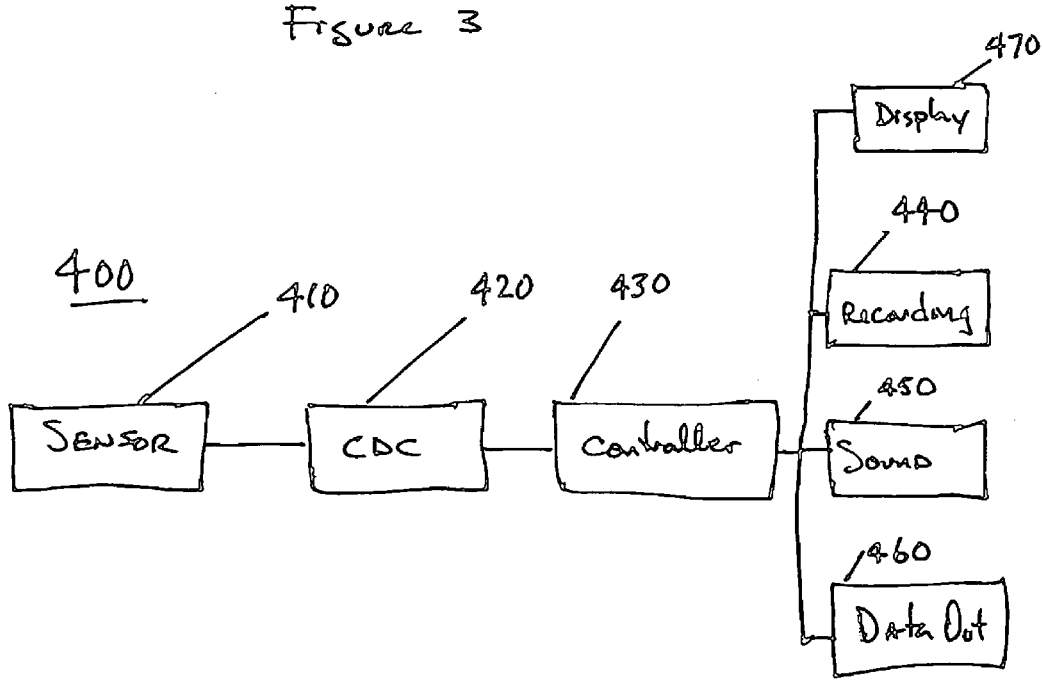
FIG. 4 is a block diagram of one embodiment of an apparatus for monitoring physiological conditions.

FIG. 2 shows a sensor 200 that has been coupled, using an elastic band 260, to a blood vessel 240 of a patient's arm 250. In FIG. 2, the heart is "resting" in diastole and the blood vessel 240 is not particularly engorged with blood. After the sensor 200 is coupled to the blood vessel 240, an electric potential can be placed across the first plate 210 and second plate 230 of the sensor. This electrical potential can come from, for example, a battery or other power source that is connected to the sensor using a port 270. On embodiment of the invention, as seen in FIG. 4, uses a capacitive to digital converter 420 and a controller 430 to detect an initial capacitance generated in response to impressing the potential across the sensor. This initial capacitance is, for example, a baseline capacitance.

Figure 3:
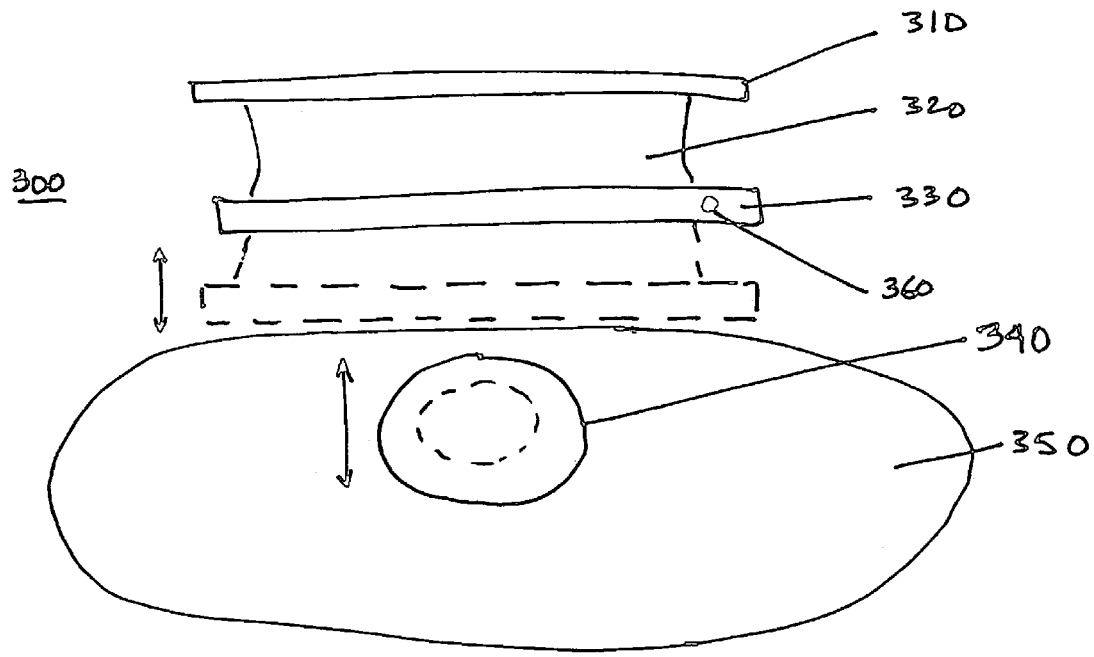
FIG. 3 is a side view of an alternative embodiment of a capacitive sensor.

FIG. 3, shows a blood vessel 340 that is engorged with blood due to the systolic period whereby the heart is contracting. The second plate 330 of the sensor 300 has been forced towards the first plate 310 by the engorged blood vessel 340. The previously mentioned capacitive to digital converter 420 and a controller 430 can then detect a first capacitance generated in response to the pressure from the engorged vessel 340. As seen below, this newly detected capacitance can be used to determine a physiological measurement (e.g., blood pressure, pulse rate) of the patient.

A person of ordinary skill in the art will be familiar with capacitive sensors such as the sensor 300 in FIG. 3. In brief, capacitive sensors turn capacitance variation into a voltage, frequency or pulse width variation. Such sensors have been used, for example, to construct light dimmer switches or devices that locate wall studs. Capacitive sensors are described in an article by Larry Baxter entitled "Capacitive Sensors"; www.capsense.com/capsense-wp.pdf; copyright Jun. 26, 2000, revised Jul. 20, 2000; pages 1-17, which is hereby incorporated by reference. Variations in capacitance can be derived in many different ways. For example, capacitance changes when the distance between two capacitive plates change. When plates, such as plates 310 and 330 in FIG. 3, are parallel and displaced by a change in distance (d), the change in capacitance (c) is obtained as follows:

$$\frac{\Delta C}{\Delta d} = -\varepsilon_0 \varepsilon_r \frac{A}{d^2}$$

where A is area. However, capacitance also changes when the area of overlap between two capacitive plates change. Furthermore, changes in capacitance can occur when one plate rotates in relation to another plate. Thus, the invention described herein is not limited to any one manner of measuring changes in capacitance. For example, changes in capacitance can be monitored when the second plate 330 moves towards the first plate 310. However, as another example, a change in capacitance also occurs when the second plate 330 slides parallel to the first plate 310.

Capacitive sensors, such as the sensor embodiment shown in FIG. 3, can be used to monitor, for example, physiological measurements such as blood pressure. In one embodiment of the invention, a user can first measure his baseline blood pressure (Baseline BP) using a using a manometer such as a sphygmomanometer. Then, the sensor can be coupled to patient's wrist and, upon detecting a first pulsatile event from the blood vessel, the CDC 420 and controller 430 can detect a first minimum capacitance generated in response to the first pressure or pulse. As those of ordinary skill in the art will appreciate, finding minimum values is well known in the art and can be accomplished by determining, for example, a change in slope of physiological data (i.e., negative slope to positive slope). The invention can also detect a first maximum capacitance generated in response to said first pressure. Again, those of ordinary skill in the art will appreciate that finding maximum values is well known in the art and can be accomplished by calculating, for example, changes in slope of physiological data. The CDC 420 and controller 430 can then detect a baseline peak-to-peak blood pressure (Baseline peak-to-peak BP) by determining the difference between the first minimum capacitance and first maximum capacitance.

Continuing with the above blood pressure monitoring process, when a second pulse occurs in the blood vessel 340, the above sequence is repeated and the CDC 420 and controller 430 can detect a second minimum capacitance, a second maximum capacitance and another peak-to-peak blood pressure (New peak-to-peak BP) by determining the difference between said second minimum capacitance and said second maximum capacitance. The CDC 420 and controller 430 can then detect a new blood pressure (New BP) from the equation: (New BP)=(Baseline BP)*(New peak-to-peak BP)/(Baseline peak-to-peak BP).

This new blood pressure can be output from the controller 430 in several different ways. As seen in FIG. 4, the controller 430 can be coupled to a recorder 440 (e.g., memory), alarm 450 or external data feed 460. In some embodiments, the controller 430 can be coupled to a display 470 that can be worn, for example, on a patient's wrist as a watch. As those of ordinary skill in the art appreciate, the CDC 420 can be separate or apart from the controller 430. The CDC, in one embodiment, is a 24-Bit Capacitance-to-Digital Converter with Temperature Sensor, model AD7746, available from Analog Devices, One Technology Way, P.O. Box 9106, Norwood, Mass. 02062-9106, (781) 329-4700. The datasheet for this device, rev. 0, copyright 2005, is available from Analog Devices and is hereby incorporated by reference. A person of ordinary skill in the art can use the datasheet to implement the CDC in the invention described herein. The datasheet describes, for example, excitation frequency, serial interface, pin configurations, register descriptions, circuit descriptions, and typical applications.

Because the invention can monitor blood pressure non-invasively (e.g., coupling the sensor to a patient's wrist), an embodiment of the invention can monitor blood pressure in a substantially continuous manner. For example, blood pressure could be monitored while a patient is sleeping or taking a shower because there are no needles or pressure cuffs in or on the patient. Also, the blood pressure can be conveniently monitored for longer periods of time.

Another embodiment of the invention can detect blood pressure using a "moving window" approach. For example, after detecting a first capacitance from a first pulse event (see above), the invention can detect a second capacitance generated in response to a second pressure from a second pulse from the pulsating blood vessel. The blood pressure can then be calculated using an average blood pressure from the two most recent pulse events. A person of ordinary skill in the art will understand that the window can be enlarged to comprise, for example, ten pulse events. The average blood pressure based on ten pulse events, rather than two pulse events, will be more stable and less prone to large deviations due to electronic noise or other anomalous signal activity.

While blood pressure calculations have been discussed at length above, some embodiments of the invention calculate physiological measurements that include pulse rate. For example, as seen in FIG. 10, the sensor is activated 1000 and then total sensor capacitance is calculated 1010. The sensor can then be bound to the umbilical cord 1020 using a band or clamp. The increased capacitance due to the clamping or banding is then calculated 1030. Then, pulse data is gathered and filtered 1040. For example, after detecting a first capacitance from a first pulse event, the invention can detect a second capacitance generated in response to a second pressure from a second pulse from said pulsating blood vessel. The pulse data is compared to a threshold value to determine when a pulse "event" has occurred 1050. In other words, a pulse event can be "registered" once a certain capacitance threshold is exceeded. Consequently, two pulse events can be detected when a minimum capacitive threshold is detected two times. These detected events, coupled with the time that occurred between the two pulse events, can be used to calculate pulse rate. In one embodiment of the invention, an audible alarm is sounded to coincide with the sensed pulse 1060.

In an alternative embodiment of the invention, some of the aforementioned steps may be omitted. For example, steps 1010 and 1030 may be omitted from the process disclosed in FIG. 10. As another example, the invention previously discussed in relation to FIG. 2 does not necessarily have to detect an initial capacitance that has been generated in response to a step of impressing a potential across the first and second plates of the sensor.

Figure 9A:
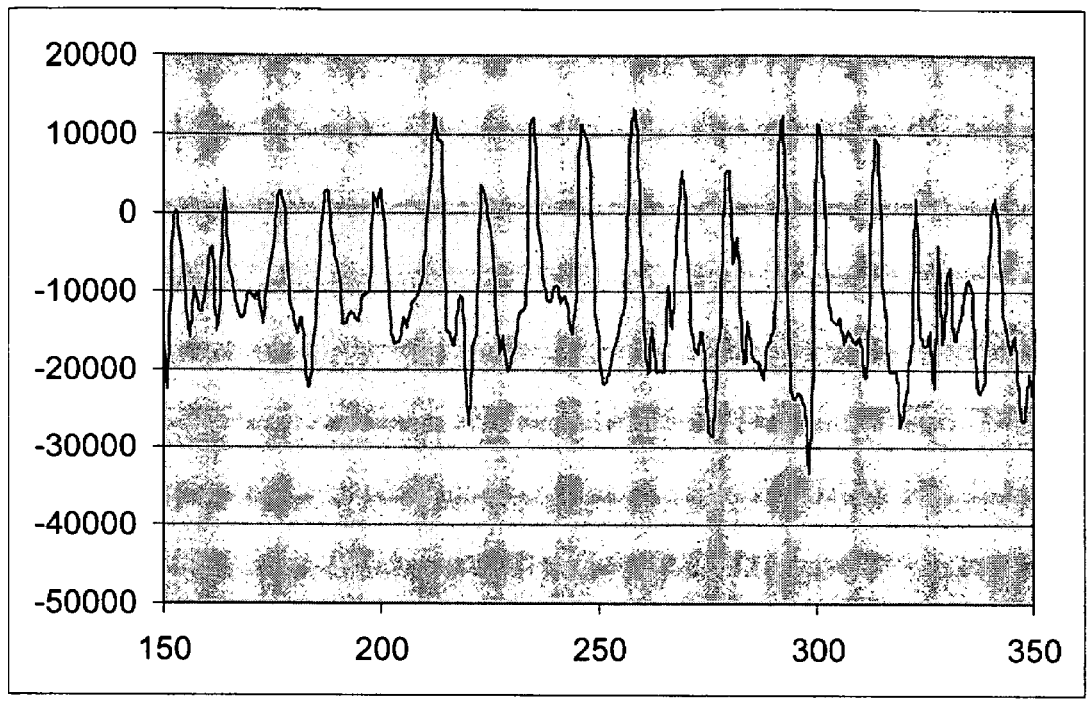
FIGS. 9a and 9b are graphs illustrating physiological data acquired using one embodiment of a capacitive sensor.
Figure 9B:
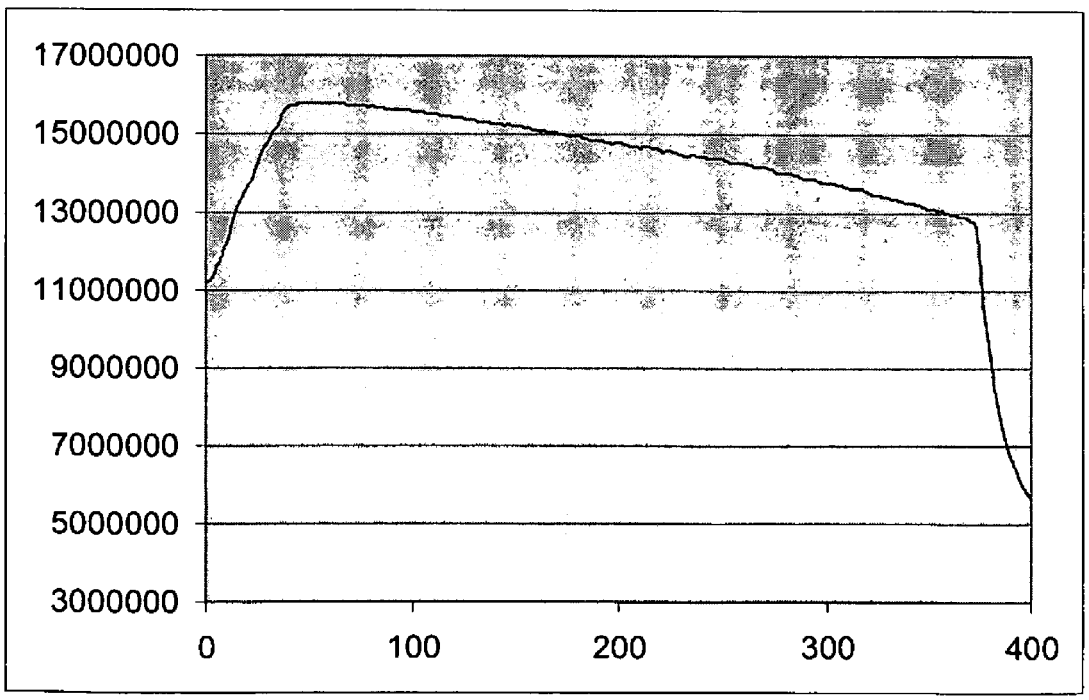
Figure 1D:
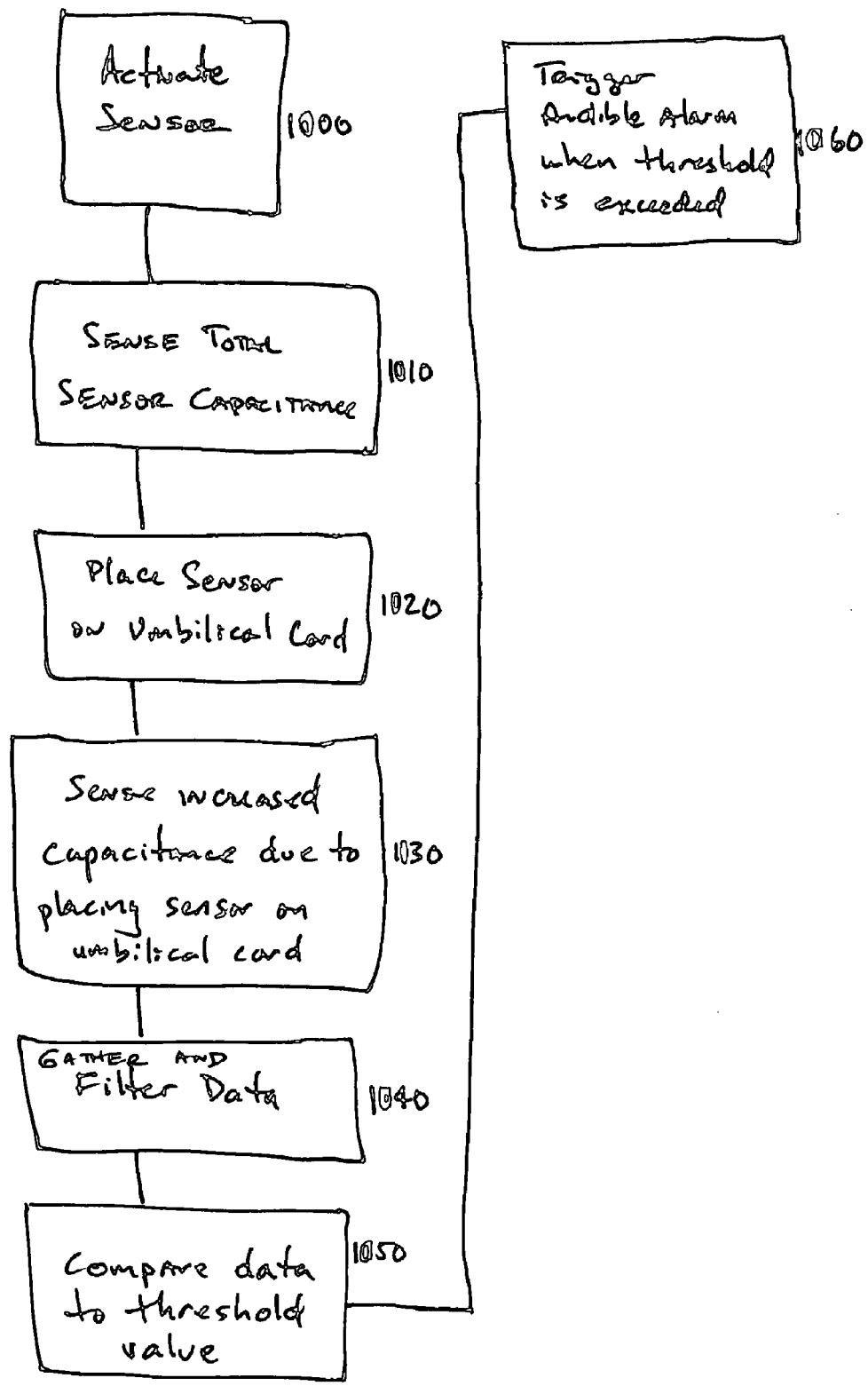

FIGS. 9a and 9b illustrate data that was gathered using an embodiment of the invention. The X axis corresponds to time sample points. The Y axis corresponds to capacitance sample points. The "HP" data in FIG. 9a is blood pressure data that has been subjected to high pass filtering, a methodology well known to those of ordinary skill in the art. FIG. 9a shows how blood pressure can be tracked using an embodiment of the invention. The blood pressure data can be used to monitor a patient's systolic blood pressure, diastolic blood pressure and mean arterial pressure. In addition, when the data exceeds a threshold value, a "pulse" can be recognized to generate pulse rate data.

The "LP" data in FIG. 9b is blood pressure data that has been subjected to low pass filtering, a methodology well known to those of ordinary skill in the art. The "LP" data is shown graphically in FIG. 9b. As those of ordinary skill in the art will appreciate, the low pass data can be removed from the original data to derive the high pass data.

Various embodiments of the invention can be used to monitor physiological measurements taken from pulsating blood vessels that are substantially located in, for example, the patient's head (e.g., temporal artery), arm (e.g., brachial, ulnar, radial), torso (e.g., aorta) or leg. Furthermore, the invention has clear applications in, for example, veterinary medicine in addition to human medicine.

In addition, embodiments of the invention can be used to calculate particular blood pressure values such as systolic blood pressure, diastolic blood pressure and mean arterial pressure. From these readings, alternative embodiments of the inventions can calculate cardiovascular abnormalities such as arrhythmias (e.g., bradyarrhythmias, tachycardias). For example, if the number of pulse events in a given period of time exceed a threshold value, the controller 430 can sound an alarm indicating, for example, a tachycardia is present.

One particular embodiment of the invention involves coupling the sensor to an umbilical cord. As the sensor is strapped to the cord, the sensor can detect pulse events and sound an alarm or beep along with every pulse. Thus, the surgical team will quickly appreciate whether there is a rapid or fading pulse in the umbilical cord without having to allocate a team member to manually detect the pulse. Embodiments of the invention can be lightweight (e.g., less than 10 ounces) and low-cost. Due to the low cost of the invention, embodiments of the invention can be disposable, thus saving sterilization costs for the hospital.

Figure 5:
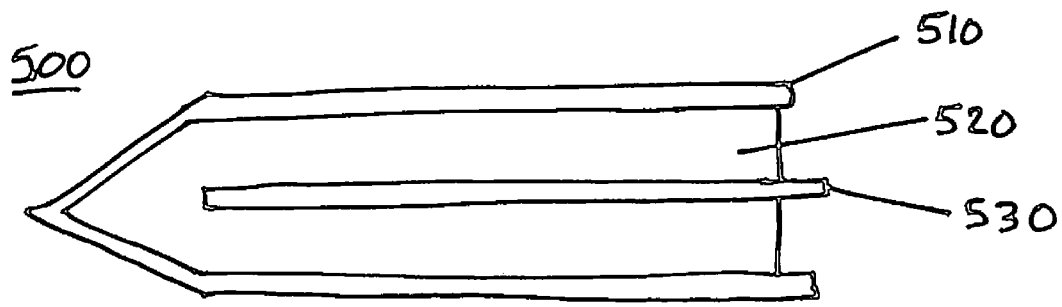
FIG. 5 is a side view of an alternative embodiment of a capacitive sensor.

The sensor itself can be constructed in many different embodiments. For example, FIG. 5 illustrates another embodiment of a capacitive sensor 500 used in the invention. In this embodiment, the sensor's first plate 510 is tubular, enclosed at one end, and substantially surrounds the sensor's second plate 520. As those of ordinary skill in the art will understand, a first plate 510 configured in this manner can provide shielding advantages over other configurations. For example, the first plate 510, acting as a Faraday cage, can be coupled to the shielding portion of a coaxial cable. A first plate 510 so constructed will eliminate or at least reduce stray capacitance or crosstalk from other circuits. The coaxial cable then couples the plates 510, 520 to a CDC.

Figure 6:
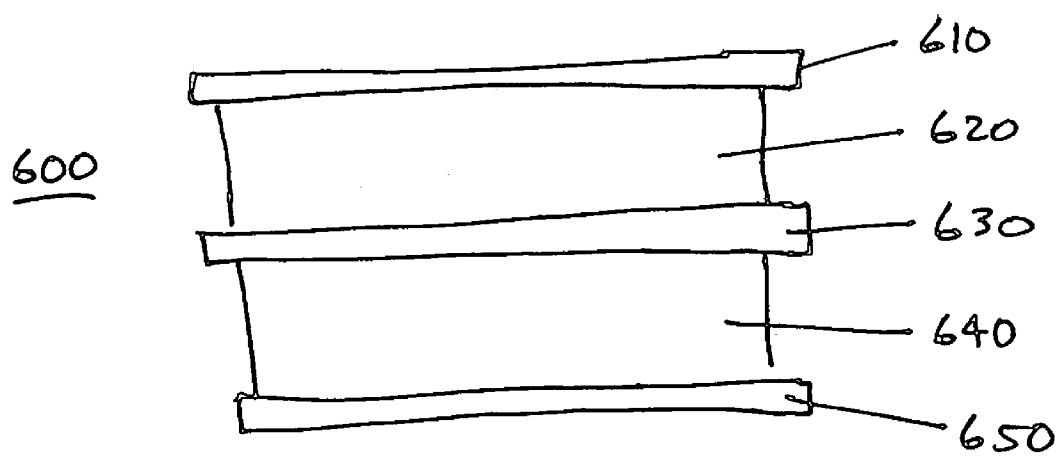
FIG. 6 is a side view of an alternative embodiment of a capacitive sensor.

FIG. 6 illustrates yet another embodiment of a capacitive sensor 600 used in the invention. In this embodiment, the sensor comprises a third plate 650. As those of ordinary skill in the art will understand, the use of multiple plates 610, 630, 650 can, for example, increase sensor capacitance, provide first-order compensation for tilt, and make shielding easier. In addition, embodiments with three or more plates can calculate differential measurements. Differential measurements can reduce or eliminate common-mode influences on the sensor. For example, if the sensor is coupled to a user's wrist and is moved while measurements are being taken, the movement would be common to the plates. The capacitance change would be common to the plates and could thereby be removed. In addition, adding a third plate can double sensor capacitance which can, as a consequence, increase capacitance measurement accuracy. For example, two capacitances are formed with a three plate sensor. One capacitance ($C_A$) can be formed between the plates 610 and 630. Another capacitance ($C_B$) can be formed between plates 630 and 650. An amplifier circuit located, for example, in a controller, can generate a voltage proportional to, for example, ($C_A-C_B$) or ($C_A/C_B$) or [($C_A-C_B$)/($C_A+C_B$)]. Dielectric mediums 620, 640 can be interspaced between the plates 610, 630, 650. Alternative embodiments of the invention can include four or more plates per sensor.

Figure 12:
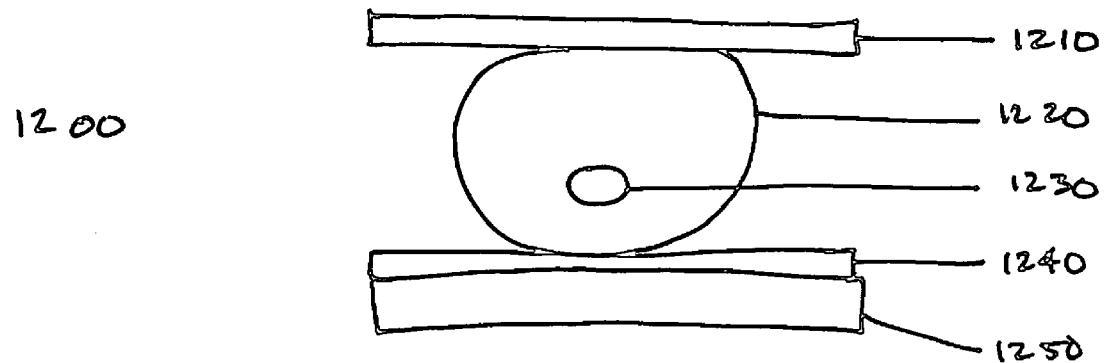
FIG. 12 is a side view of an alternative embodiment of a capacitive sensor.

FIG. 12 illustrates yet another embodiment of a capacitive sensor 1200 used in the invention. In this embodiment, the sensor comprises a first plate 1210 and a second plate 1250 with a dielectric medium 1240 between the first and second plates 1210, 1250. A patient's arm 1220 and artery 1230 can also be located between the first and second plates 1210, 1250. Thus, the capacitive plates in this invention are not limited to any one orientation in relation to the blood vessel being monitored. In other words, all of the plates in a sensor can be located on one side of an artery. However, in other embodiments of the invention, the plates can be located on multiple sides of the artery.

Figure 13:
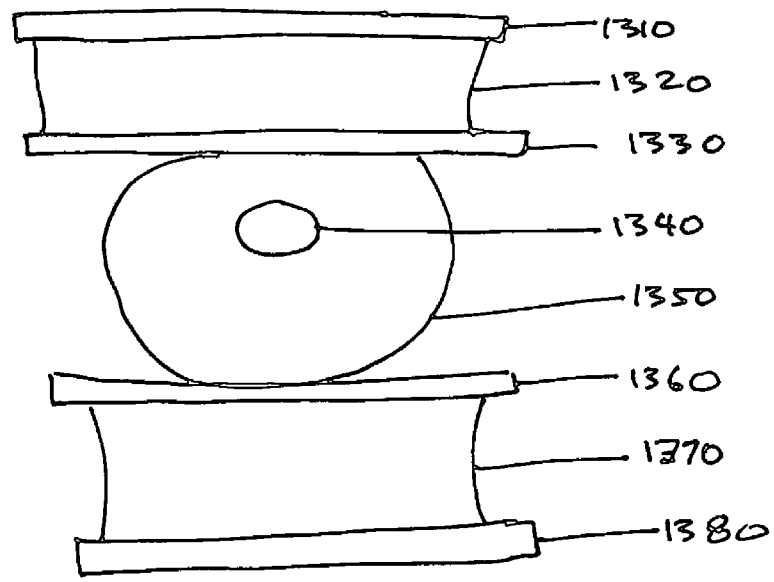
FIG. 13 is a side view of an alternative embodiment of the invention implementing two capacitive sensors.

FIG. 13 illustrates yet another embodiment of the invention using two capacitive sensors. In this embodiment, the first sensor comprises a first plate 1310 and a second plate 1330 with a dielectric medium 1320 between the first and second plates 1310, 1330. The second sensor comprises a third plate 1360 and a fourth plate 1380 with a dielectric medium 1370 between the third and fourth plates 1360, 1380. A patient's arm 1350 and artery 1340 can also be located between the first and second sensors. Pulses in the artery can be detected using changes in capacitance in the first and/or second sensors. To better illustrate the advantages of such an embodiment, the following example is provided. An artery can twist as it progresses along the umbilical cord. At one location in the cord, the artery is closer to the right wall of the cord. Further along the cord, the artery may be closer to the left wall of the cord. An embodiment with multiple sensors located in, for example, a ring configuration, may be better able to detect pulse activity in the vessel regardless of where the umbilical cord may be located (e.g., right side of the cord). A person of ordinary skill in the art will understand that using multiple sensors can provide for more accurate measurements.

Figure 7:
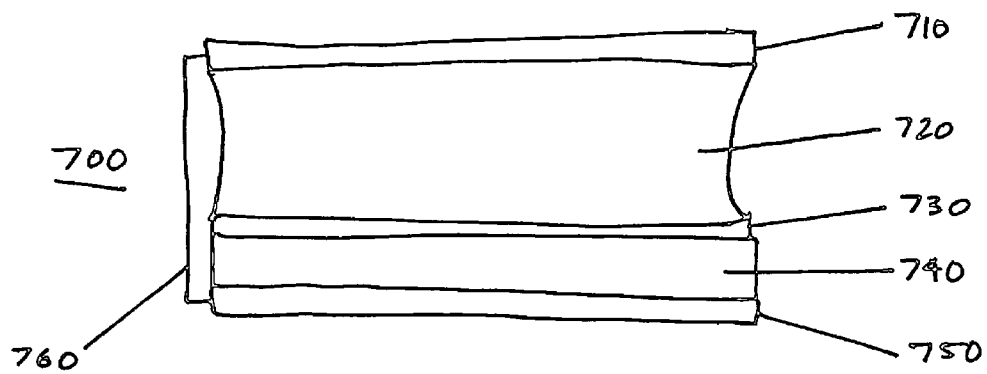
FIG. 7 is a side view of an alternative embodiment of a capacitive sensor.

FIG. 7 illustrates another embodiment of a capacitive sensor 700 used in the invention. In this embodiment, the sensor's first plate 710 is coupled to a dielectric 720 (e.g., compressible foam). Dielectric 720 is coupled to the sensor's second plate 730. The second plate 730 is coupled to a printed circuit board 740, which is also coupled to a third plate 750. The first plate 710 is also coupled to the third plate 750 using one or more vias 760. As one of ordinary skill in the art will understand, the third plate 750 can function as a shield. The first plate 710 can be operatively coupled to a patient's blood vessel. The first plate 710 can be acted upon by the pulsating blood vessel to generate multiple capacitances to monitor, for example, blood pressure or pulse rate.

Figure 8:
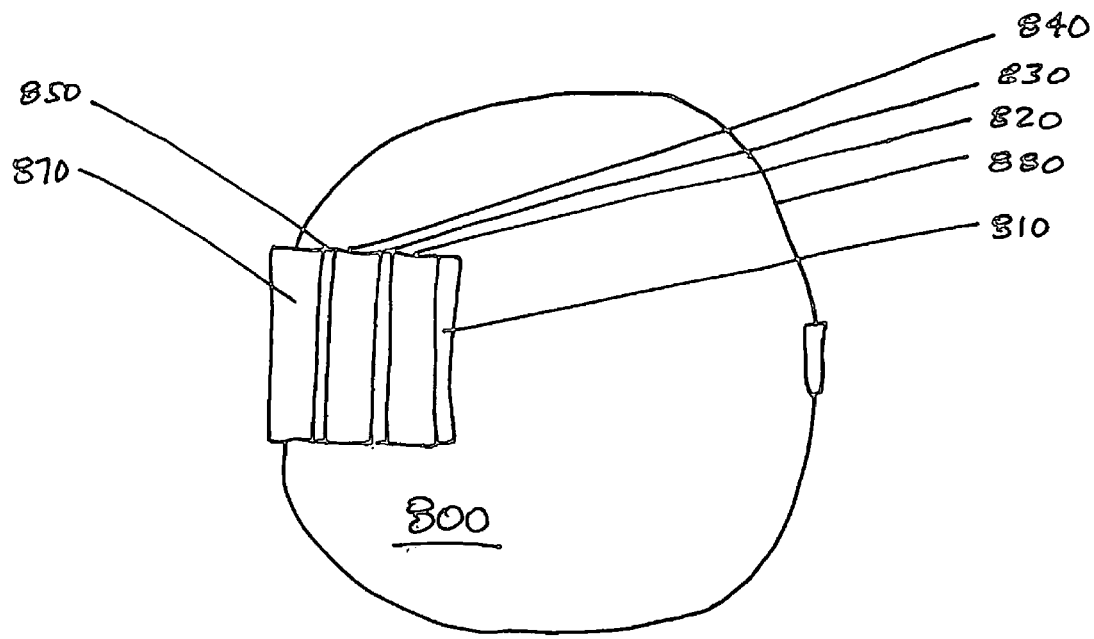
FIG. 8 is a side view of an alternative embodiment of a capacitive sensor.

FIG. 8 discloses another embodiment of the invention wherein the embodiment disclosed in FIG. 7 is affixed to a watch. For example, the third plate 850 can be operatively coupled to a watch-face 870. The watch wristband 880 could hold the first plate 810 and sensor 800 against the patient's wrist. The sensor 800 could then relay information to a CDC and controller coupled to the wristwatch 870. Consequently, a user could continuously monitor, for example, his pulse rate and/or blood pressure. Referring to FIG. 4, the user could monitor his blood pressure by viewing a readout on a display 470. Also, if the blood pressure exceeds a limit, an alarm 450 can sound. Furthermore, upon the blood pressure exceeding the limit, an event recorder 440 can be triggered to record abnormal heart rates.

As those of ordinary skill in the art will appreciate, one embodiment of the invention's controller 430 can have software or one or more program storage media readable by a machine (as will be described in more detail below). The media can contain instructions that are executed by a processor for performing various steps described above. For example, software can help detect an initial capacitance generated in response to applying a potential across the first and second plates of a sensor. The software can also help detect a first capacitance generated in response to a first pressure from a first pulse from the pulsating blood vessel. The software can detect a physiological measurement of said patient in response to detecting said second capacitance.

While various examples have been described above for monitoring physiological conditions of a user, one of ordinary skill in the art will realize that any number of apparatuses and methods can be provided for monitoring such conditions and that those apparatuses and methods are encompassed within the scope of the present invention. In addition, those of ordinary skill in the art will appreciate that there are a number of alternative configurations, not specifically mentioned above, for (i) constructing capacitive sensors and for (ii) operatively coupling such sensors to blood vessels for monitoring purposes, and that such embodiments are within the scope of the present invention.

Figure 14:
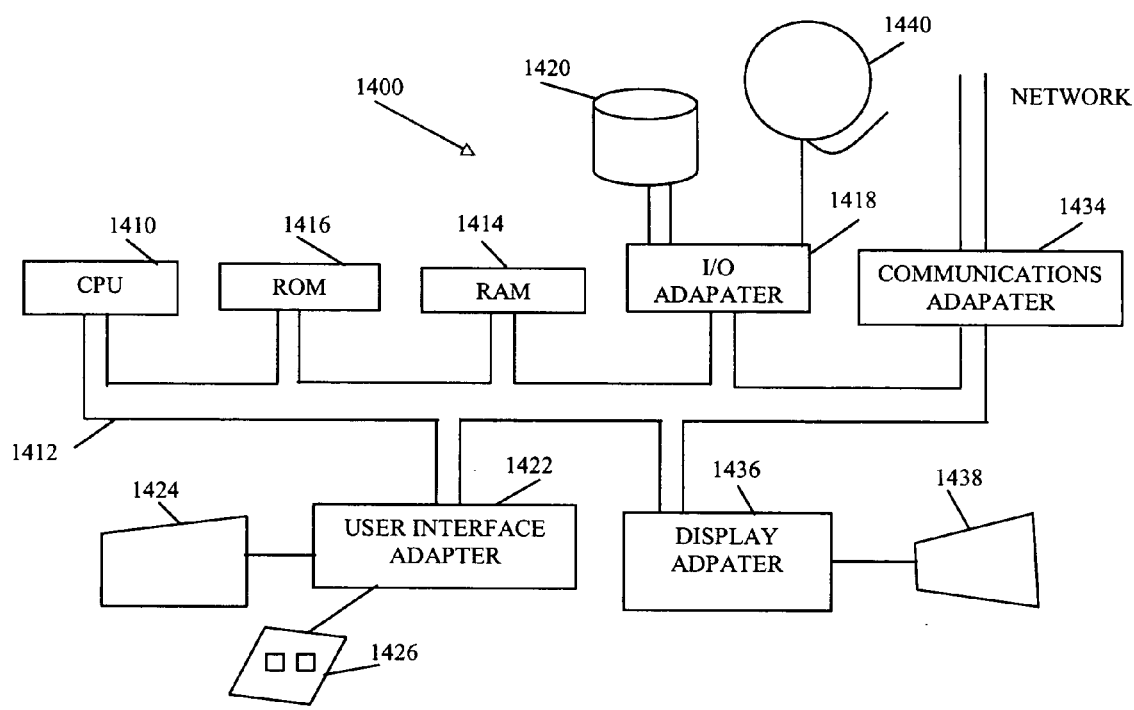
FIG. 14 is a block diagram of one embodiment of a data processing system.
Figure 15:
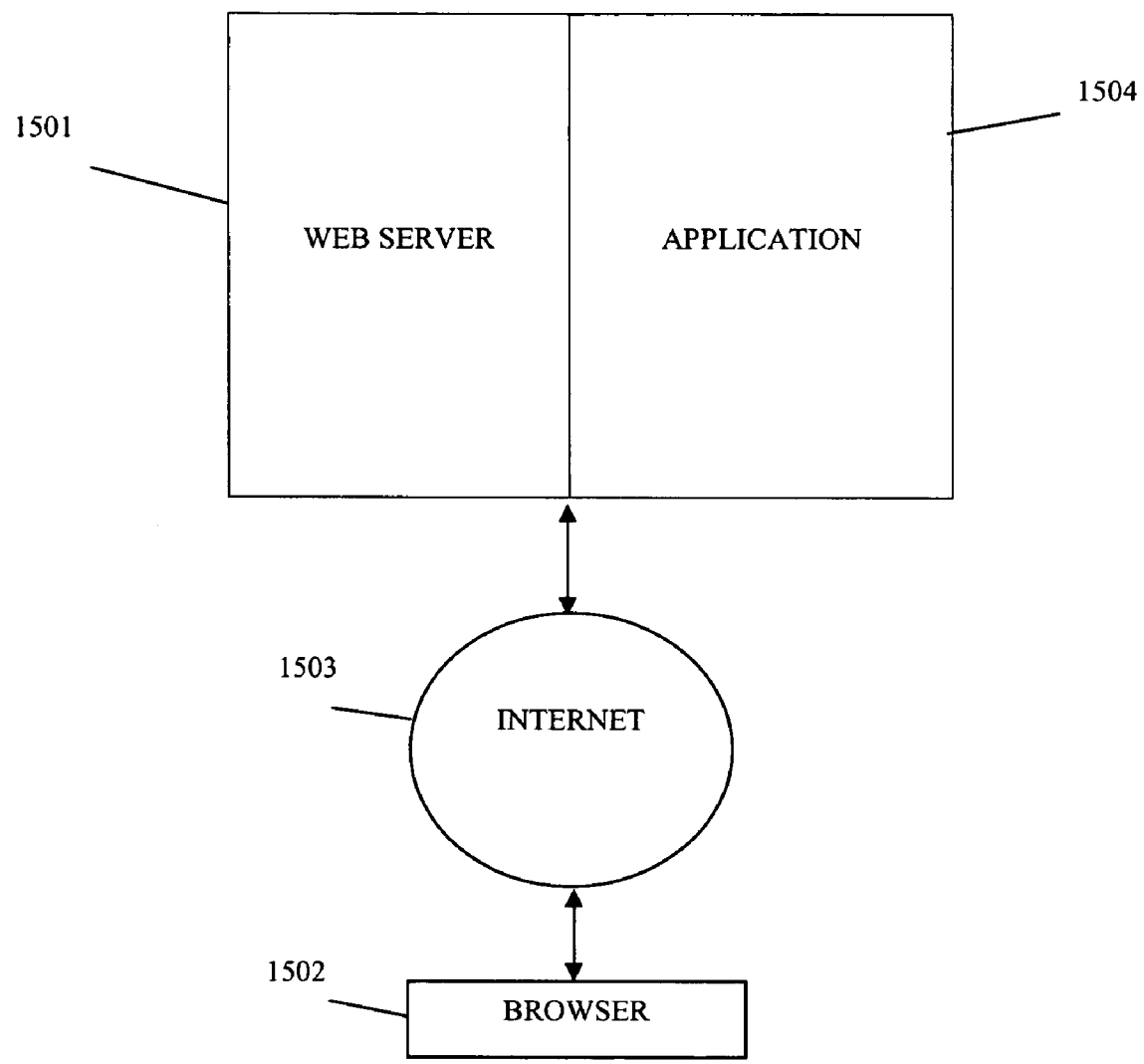
FIG. 15 is a block diagram of one embodiment of a data processing environment.

Referring to FIG. 14, an example is shown of a data processing system 1400, which can be used for implementing any of the aforementioned embodiments of the invention, including one or more of the client machines 1502 and the web server 1501 (FIG. 15). The system has a central processing unit (CPU) 1410, which is coupled to various other components by system bus 1412. Read only memory ("ROM") 1416 is coupled to the system bus 1412 and includes a basic input/output system ("BIOS") that controls certain basic functions of the data processing system 1400. Random access memory ("RAM") 1414, I/O adapter 1418, and communications adapter 1434 are also coupled to the system bus 1412. I/O adapter 1418 can be a small computer system interface ("SCSI") adapter that communicates with a disk storage device 1420. Communications adapter 1434 interconnects bus 1412 with an outside network enabling the data processing system to communicate with other such systems. Input/Output devices are also connected to system bus 1412 via user interface adapter 1422 and display adapter 1436. Keyboard 1424 and mouse 1426 are interconnected to bus 1412 via user interface adapter 1422. Display adapter 1436 connects display monitor 1438 to system bus 1412. In this manner, a user is capable of inputting to the system throughout the keyboard 1424 or mouse 1426 and receiving output from the system via display 1438.

In one embodiment of the invention, the controller 430 (FIG. 4) may include the CDC 420 and other components such as, for example, a battery, a CPU 1410 (FIG. 14), bus 1412, ROM 1416, BIOS, RAM 1414, I/O adapter 1418, communications adapter 1434, disk storage device 1420, display adapter 1436 and a display monitor 1438. The sensor 410 can interface the user interface adapter 1422. In one embodiment of the invention, the sensor 410 and controller 430 are sold separately. In other embodiments, the sensor 410 and controller 430 are sold as a unit. The sensor 410 and controller 430 can share one housing in certain embodiments of the invention. For example, the sensor 410 and controller 430 may share one housing that is strapped, via an elastic band, to the umbilical cord of a child. In alternative embodiments of the invention, rigid or semi-rigid bands may be used.

Embodiments of the invention can be implemented as a computer system programmed to execute the method or methods described herein, and as a computer program product. According to the computer system implementation, sets of instructions for executing the method or methods are resident in the random access memory 1414 of one or more computer systems configured generally as described above. Those of ordinary skill in the art will appreciate that the computer program product or software program instructions are capable of being distributed as one or more program products, in a variety of forms. Processor 1410, from either a client machine 1502 and/or server computer 1501, can execute one or more of the computer program products stored in memory 1414. Client computer 1502 and server computer 1501 can be individually programmed to collectively execute the process or processes of the invention described herein. Until required by the computer system, the set of instructions can be stored as a computer program product in another computer memory, for example, in disk drive 1420 (which can include a removable memory such as an optical disk or floppy disk for eventual use in the disk drive 1420). Further, the computer program product can also be stored at another computer and transmitted when desired to the user's workstation by a network or by an external network such as the Internet. One of ordinary skill in the art would appreciate that the physical storage of the sets of instructions physically changes the medium upon which it is stored so that the medium carries computer readable information. The change can be electrical, magnetic, chemical, biological, or some other physical change. While it is convenient to describe the invention in terms of instructions, symbols, characters, or the like, the reader should remember that all of these and similar terms should be associated with the appropriate physical elements.

As yet another embodiment of the invention, an embodiment of the invention entails a networked data processing environment. The data processing environment is an arrangement, as previously described, of one or more client computers 1502 and server computers 1501 (generally "hosts") connected to each other by a network 1503, for example, the Internet. One of ordinary skill in the art will recognize that, for example, WiFi, satellite communication and the like can constitute a network. Users access information and interface with network 1503 and server computer 1501 through a client computer 1502.

Note that the invention can describe terms such as comparing, validating, selecting, identifying, or other terms that could be associated with a human operator. However, for at least a number of the operations described herein, which form part of at least one of the embodiments, no action by a human operator is required. The operations described are, in large part, machine operations processing electrical signals to generate other electrical signals.

Additionally, the foregoing detailed description has set forth various embodiments of the present invention via the use of block diagrams, flowcharts, and/or examples. It will be understood by those of ordinary skill in the art that each block diagram component, flowchart step, and operations and/or components illustrated by the use of examples can be implemented, individually and/or collectively, by a wide range of hardware, software, firmware, or any combination thereof. The present invention can be implemented as those of ordinary skill in the art will recognize, in whole or in part, in standard Integrated Circuits, Application Specific Integrated Circuits (ASICs), as a computer program running on a general-purpose machine having appropriate hardware, such as one or more computers, as firmware, or as virtually any combination thereof and that designing the circuitry and/or writing the code for the software or firmware would be well within the skill of one of ordinary skill in the art, in view of this disclosure. It will also be understood that certain of the above-described structures, functions and operations of the above-described embodiments are not necessary to practice the present invention and are included in the description simply for completeness of an example embodiment or embodiments. In addition, it will be understood that specific structures, functions and operations set forth in the above-referenced patents and publications can be practiced in conjunction with the present invention, but they are not essential to its practice. It is therefore to be understood that within the scope of the claims, the invention can be practiced otherwise than as specifically described without actually departing from the spirit and scope of the present invention. Finally, all patents, publications and standards referenced herein are hereby incorporated by reference.

What is claimed is:

1. A method for determining a physiological measurement comprising the following steps:
bounding a capacitive sensor to a pulsating blood vessel of an umbilical cord of a patient;
said sensor including a first plate, a second plate, and a dielectric medium operatively coupled to said first plate and said second plate;
said dielectric medium including a material that enables said first plate and said second plate to move relative to one another when pressure from said pulsating blood vessel is exerted on said second plate;
detecting a first capacitance generated in response to a first pressure from a first pulse from said pulsating blood vessel; wherein said first pressure is exerted against said second plate of said sensor; and
detecting a physiological measurement of said patient, by a controller, in response to detecting said first capacitance.

2. The method of claim 1, wherein said step of detecting said physiological measurement includes detecting a blood pressure of said patient.

3. The method of claim 2, wherein said step of detecting said blood pressure is performed for more than 1 hour in a substantially continuous manner.

4. The method of claim 2, wherein said step of detecting said blood pressure further comprises the following steps:
detecting a second capacitance generated in response to a second pressure from a second pulse from said pulsating blood vessel, wherein said second pressure is exerted against said second plate of said sensor; and detecting said blood pressure using a moving window comprised of said first capacitance and said second capacitance.

5. The method of claim 1, wherein said step of operatively coupling said capacitive sensor to said pulsating blood vessel is performed non-invasively.

6. The method of claim 1, wherein said step of detecting said physiological measurement includes detecting a pulse rate of said patient.

7. The method of claim 6, further comprising the following steps:

detecting a second capacitance generated in response to a second pressure from a second pulse from said pulsating blood vessel, wherein said second pressure is exerted against said second plate of said sensor; and detecting said pulse rate in response to detecting said first capacitance and detecting said second capacitance.

8. The method of claim 1, wherein said pulsating blood vessel is substantially located in a part of the patient's body chosen from the group consisting of said patient's head, arm, torso and leg.

9. One or more program storage media readable by a machine and containing instructions for performing the following steps of the method contained in claim 1:

detecting a first capacitance generated in response to a first pressure from a first pulse from said pulsating blood vessel; wherein said first pressure is exerted against said second plate of said sensor; and detecting a physiological measurement of said patient in response to detecting said first capacitance.

10. The method of claim 1, further comprising the following steps:

impressing an electric potential across said first and second plates of said sensor; and detecting an initial capacitance generated in response to said step of impressing said potential across said first and second plates of said sensor.

11. A method for determining a physiological measurement comprising the following steps:

operatively coupling a capacitive sensor to a pulsating blood vessel of a patient;

said sensor including a first plate, a second plate, and a dielectric medium operatively coupled to said first plate and said second plate;

said dielectric medium including a material that enables said first plate and said second plate to move relative to one another when pressure from said pulsating blood vessel is exerted on said second plate;

detecting a first capacitance generated in response to a first pressure from a first pulse from said pulsating blood vessel; wherein said first pressure is exerted against said second plate of said sensor;

detecting a physiological measurement of said patient by a controller in response to detecting said first capacitance, wherein said step of detecting said physiological measurement includes detecting a blood pressure of said patient;

detecting a baseline blood pressure (Baseline BP) using a manometer;

detecting a first minimum capacitance generated in response to said first pressure;

detecting a first maximum capacitance generated in response to said first pressure;

detecting a baseline peak-to-peak blood pressure (Baseline peak-to-peak BP) by determining a difference between said first minimum capacitance and said first maximum capacitance;

detecting a second minimum capacitance generated in response to a second pressure from a second pulse from said pulsating blood vessel, wherein said second pressure is exerted against said second plate of said sensor;

detecting a second maximum capacitance generated in response to said second pressure;

detecting a new peak-to-peak blood pressure (New peak-to-peak BP) by determining a difference between said second minimum capacitance and said second maximum capacitance; and detecting a new blood pressure of said patient (New BP) from the equation: (New BP)=(Baseline BP)*(New peak-to-peak BP)/(Baseline peak-to-peak BP).

12. A method for determining a physiological measurement comprising the following steps:

operatively coupling a capacitive sensor to a pulsating blood vessel of a patient;

said sensor including a first plate, a second plate, and a dielectric medium operatively coupled to said first plate and said second plate;

said dielectric medium including a material that enables said first plate and said second plate to move relative to one another when pressure from said pulsating blood vessel is exerted on said second plate;

detecting a first capacitance generated in response to a first pressure from a first pulse from said pulsating blood vessel; wherein said first pressure is exerted against said second plate of said sensor; and detecting a physiological measurement of said patient by a controller in response to detecting said first capacitance;

wherein said pulsating blood vessel is substantially located in said patient's umbilical cord.

13. A system comprising:

one or more memory units operable for storing one or more computer program products for detecting a physiological measurement;

one or more processors coupled to the one or memory units, wherein the one or more processors execute the one or more computer program products for performing the steps of:

detecting a first capacitance generated in response to a first pressure from a first pulse from a pulsating blood vessel of a patient; wherein said first pressure is exerted against a capacitive sensor that is operatively coupled to said pulsating blood vessel;

detecting a physiological measurement of said patient in response to detecting said first capacitance, wherein said step of said one or more processors executing the one or more computer products for detecting said physiological measurement includes detecting a blood pressure of said patient;

storing a baseline blood pressure (Baseline BP) detected using a manometer;

detecting a first minimum capacitance generated in response to said first pressure;

detecting a first maximum capacitance generated in response to said first pressure;

detecting a baseline peak-to-peak blood pressure (Baseline peak-to-peak BP) by determining a difference between said first minimum capacitance and said first maximum capacitance;

detecting a second minimum capacitance generated in response to a second pressure from a second pulse from said pulsating blood vessel, wherein said second pressure is exerted against said sensor detecting a second maximum capacitance generated in response said second pressure;

detecting a new peak-to-peak blood pressure (New peak-to-peak BP) by determining a difference between said second minimum capacitance and said second maximum capacitance; and detecting a new blood pressure of said patient (New BP) from the equation: (New BP)=(Baseline BP)*(New peak-to-peak BP)/(Baseline peak-to-peak BP).

* * * * *